United States Patent [19]

Franke et al.

[11] 4,276,309
[45] Jun. 30, 1981

[54] ACYLUREA INSECTICIDES

[75] Inventors: Heinrich Franke; Hartmut Joppien, both of Berlin, Fed. Rep. of Germany

[73] Assignee: Schering AG, Berlin, Fed. Rep. of Germany

[21] Appl. No.: 167,317

[22] Filed: Jul. 10, 1980

[30] Foreign Application Priority Data

Jul. 11, 1979 [DE] Fed. Rep. of Germany ....... 2928410

[51] Int. Cl.$^3$ ........................ C07C 127/22; A01N 9/20
[52] U.S. Cl. ........................................ 424/322; 564/44
[58] Field of Search ........................... 564/44; 424/322

[56] References Cited

U.S. PATENT DOCUMENTS

| | | | |
|---|---|---|---|
| 4,013,717 | 3/1977 | Wellinga et al. | 564/44 |
| 4,089,975 | 5/1978 | Wade et al. | 564/44 X |
| 4,139,636 | 2/1979 | Sirrenberg et al. | 564/44 X |
| 4,162,330 | 7/1979 | Ehrenfreund | 564/44 X |
| 4,170,657 | 10/1979 | Rigterink | 564/44 X |

Primary Examiner—Thomas A. Waltz

Attorney, Agent, or Firm—Michael J. Striker

[57] ABSTRACT

Acylurea insecticides and methods of preparation thereof are disclosed. The acylureas have compositions of the general formula

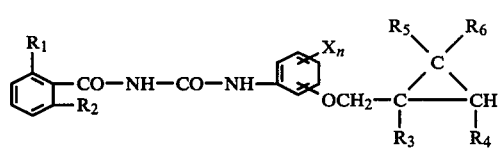

wherein $R_1$ is halogen, alkyl with from 1 to 6 carbon atoms or alkoxy with from 1 to 6 carbon atoms; $R_2$ is hydrogen or halogen; $R_3$ is hydrogen or alkyl with from 1 to 6 carbon atoms; $R_4$ is hydrogen, alkyl with from 1 to 6 carbon atoms, aryl with from 6 to 12 carbon atoms, halogen substituted aryl with from 6 to 12 carbon atoms or alkaryl with from 7 to 12 carbon atoms; $R_5$ is halogen; $R_6$ is hydrogen or halogen; X is halogen or alkyl with from 1 to 6 carbon atoms; and n is 0, 1 or 2.

52 Claims, No Drawings

ACYLUREA INSECTICIDES

DESCRIPTION

BACKGROUND OF THE INVENTION

1. Field of the Invention

This invention relates to methods of preparing acylureas, to acyl urea compositions, to insecticidal compositions and to a method of eliminating insects.

2. Brief Description of the Background of the Invention Including Prior Art

German Offenlegungsschrift DE-OS No. 2,123,236 discloses 1-acyl-3-phenyl-ureas having special insecticidal effects.

SUMMARY OF THE INVENTION

1. Purposes of the Invention

It is an object of the invention to provide an insecticide, which is more successfull in the combat of certain insects.

It is another object of the invention to to provide methods for the preparation of acylurea insecticides.

These and other objects and advantages of the invention will become evident from the description which follows.

2. Brief Description of the Invention

The present invention provides a method for preparing acylureas of the composition having the general formula

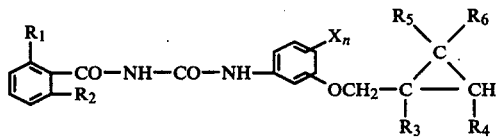

wherein
$R_1$ is halogen, alkyl with from 1 to 6 carbon atoms or alkoxy with from 1 to 6 carbon atoms;
$R_2$ is hydrogen or halogen;
$R_3$ is hydrogen or alkyl with from 1 to 6 carbon atoms;
$R_4$ is hydrogen, alkyl with from 1 to 6 carbon atoms, aryl with from 6 to 12 carbon atoms, halogen substituted aryl with from 6 to 12 carbon atoms or alkaryl with from 7 to 12 carbon atoms;
$R_5$ is halogen;
$R_6$ is hydrogen or halogen;
X is halogen or alkyl with from 1 to 6 carbon atoms; and
n is 0, 1 or 2
by contacting at suitable temperature and pressure an alkoxyaniline of the general formula

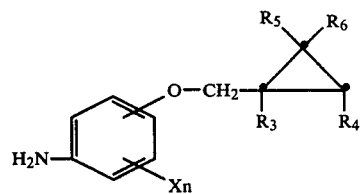

and benzoylisocyanates of the general formula

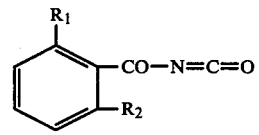

Preferably the contacting occurs in the presence of an inert organic solvent and the contacting temperature is from about 20° C. to 100° C.

Alternatively the acylureas of the composition having the general formula (1) are prepared by contacting at suitable temperature and pressure an alkoxyphenylisocyanate of the general formula

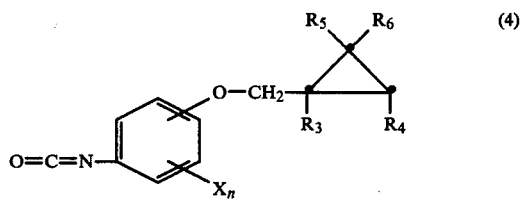

and benzamides of the general formula

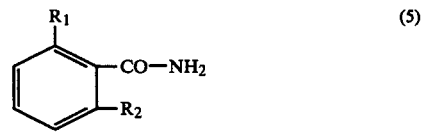

Preferably the contacting occurs in the presence of an inert organic solvent and the contacting temperature is from about 80° C. to 200° C.

Preferred acylureas according to the invention are those wherein
$R_1$ is chlorine or fluorine;
$R_2$ is chlorine, fluorine or hydrogen;
$R_3$ is hydrogen or methyl;
$R_4$ is hydrogen, methyl or phenyl;
$R_5$ is chlorine, bromine or fluorine;
$R_6$ is chlorine, bromine, fluorine or hydrogen;
X is chlorine or methyl; and
n is 0, 1 or 2.

In one aspect of the invention a composition having insecticidal activity is provided which comprises acylureas of the composition having the general formula (1) and a carrier and/or auxiliary materials. There is also provided a method of killing and/or eliminating insects by placing into the possible pathway of the insects a composition having the general formula (1). The insects can be diptera, coleoptera and/or lepidoptera.

DESCRIPTION OF INVENTION AND PREFERRED EMBODIMENTS

In accordance with the present invention an insecticide is provided containing one or several compounds of the general formula

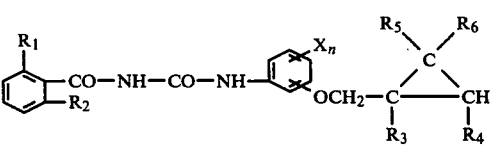

wherein
R₁ is halogen, alkyl with from 1 to 6 carbon atoms, or alkoxy with from 1 to 6 carbon atoms;
R₂ is hydrogen or halogen;
R₃ is hydrogen or alkyl with from 1 to 6 carbon atoms;
R₄ is hydrogen, alkyl with from 1 to 6 carbon atoms, aryl with from 6 to 12 carbon atoms, halogen substituted aryl with from 6 to 12 carbon atoms, or alkaryl with from 7 to 12 carbon atoms;
R₅ is halogen;
R₆ is hydrogen or halogen;
X is halogen or alkyl with from 1 to 6 carbon atoms; and
n is 0, 1 or 2.

The compositions according to the invention in comparison with other known active substances show a surprisingly superior insecticidal effect and other advantages and they combat specifically certain insects.

The compounds according to the present invention develop an extraordinary selective insecticidal activity against major insect pests especially of the orders of diptera, coleoptera and lepidoptera.

The application of the compounds of the present invention can be performed in concentrations of from about 0.001 to 5.0% and preferably from about 0.01 to 0.5%.

The compounds of the present invention can be employed solely, in mixture with each other or in mixture with other insecticidal active substances. If desired, other plant protective or pest control substances such as acaricides or fungicides can be added depending on the purpose present.

A support of the effective activity and of the speed of effectiveness can, for example, be achieved by adding effect increasing additives such as organic solvents, wetting agents and oils. Such additives therefor possibly allow a decrease in the applied concentration of the active ingredient.

It is practical to employ the active substances of the present invention and their mixtures as prepared compositions such as powders, strewing materials, granulates, solutions, emulsions or suspensions, with addition of liquid and/or solid carrier materials and possibly of wetting, adhering, emulsifying and/or dispersing agents.

Suitable liquid carrier materials include for example water, aliphatic and aromatic hydrocarbons, furthermore cyclohexanone, isophorone, dimethylsulfoxide, dimethylformamide and petroleum fractions.

As solid carrier materials are suitable mineral earths, for example tonsil, silicagel, talcum, caoline, attaclay, limestone, silica and plant products, for example flours.

As surface active ingredients are cited by way of example: calcium lignin sulfonate and its salts, phenol sulfonic acids and its salts, formaldehyde condensates, fatty alcohol sulfonates and substituted benzenesulfonic acids and their salts.

The amount of one or more active ingredients in the various compositions can be in a wide range. For example, agents comprise from about 5 to 95 weight percent active ingredients, from about 95 to 5 weight percent liquid or solid carrier materials and if desired up to about 20 weight percent of surface active ingredients.

The application of the agent can be performed in the usual way, for example with water as carrier in sprinkling liquor amounts of from about 100 to 300 liter/hectare. It is also possible to apply the agent in the so called low-volume and ultra-low-volume process and to apply it in the form of so-called microgranulates.

The preparation of these agents can be performed in a conventional manner, for example by milling and mixing processes. If desired the individual components can also be mixed shortly before their application as it is for example performed practically in the so-called tank-mix process.

The compounds according to the invention are showing a particularly preferred insecticidal effect when in the above general formula (1) R₁ is chlorine or fluorine, R₂ is chlorine, fluorine or hydrogen, R₃ is hydrogen or methyl, R₄ is hydrogen, methyl or phenyl, R₅ is chlorine, bromine or fluorine, R₆ is chlorine, bromine, fluorine or hydrogen, X is chlorine or methyl and n is 0, 1 or 2.

In general R₄ can also be a substituted aryl group. Examples for R₄ substituent groups include propyl, phenyl, naphthyl, 4-chloro-phenyl, 4-bromonaphthyl, tolyl and p-cumyl.

The compounds of the present invention can be prepared by reacting alkoxanilines of the general formula

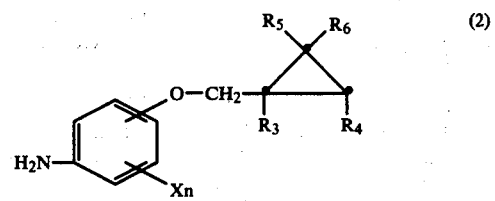

with benzoylisocyanates of the general formula

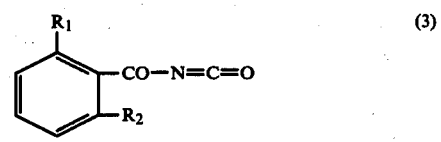

It may be desired to add a solvent ot this reaction. Alternatively, the compounds of the present invention can be prepared by reacting alkoxyphenylisocyanates of the general formula

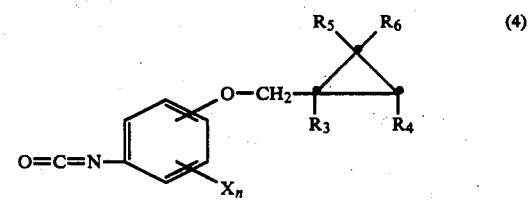

with benzamides of the general formula

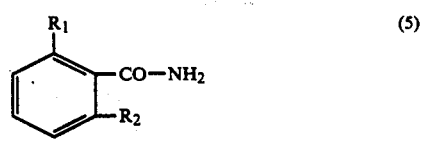

It may be desired to add a solvent to this reaction. R₁, R₂, R₃, R₄, R₅, R₆, X and n have the meaning indicated above.

Suitable solvents include those inert with respect to the reactants such as aromatic and aliphatic hydrocarbons, possibly chlorinated aromatic or aliphatic hydrocarbons, such as toluene, chlorobenzene, chloroform and hexane, ether, as diethylether and tetrahydrofurane, ester as acetic acid ethyl ester as well as nitriles as acetonitrile and benzonitrile.

The reaction temperature can vary over a wide range. Preferred for the reaction between alkoxyanilines and benzoylisocyanates are temperatures from 20° C. to 100° C. and for reaction between alkoxyphenylisocyanates and benzimides are temperatures from about 80° C. to 200° C. The reactions can be performed at atmospheric pressures.

The starting materials employed as benzamides, benzoylisocyanates, alkoxyanilines and alkoxyphenylisocyanates are known in general and can be prepared by conventional methods. The preparation of the compounds according to the invention is illustrated in Example 1.

EXAMPLE 1

1-[3-Chloro-4-(2,2-dichloro-3-methylcyclopropylmethoxy)phenyl]-3-(2,6-dichlorobenzoyl)-urea 10.39 g (0.037 mole) 3-chloro-4-(2,2-dichloro-3-methylcyclopropylmethoxy)-aniline dissolved in 50 ml dry tetrahydrofuran are stirred and 7.56 g (0.035 mole) 2,6-dichlorobenzoylisocyanate dissolved in 10 ml tetrahydrofurane are added drop by drop. The temperature rises in this process to 42° C. After two hours the product is precipitated by addition of pentane, sucked off, washed with pentane and dried.

Yield: 12.6 g=72% of theoretical 1-[3-chloro-4-(2,2-dichloro-3-methylcyclopropylmethoxy)-phenyl]-3-(2,6-dichlorobenzoyl)-urea.Fp.: 175°–177° C.

The following compounds according to the present invention can be prepared by analogy.

| Name of Compound | Physical constant |
|---|---|
| 1-[3-Chloro-4-(2,2-dichlorocyclopropylmethoxy)-phenyl]-3-(2,6-dichlorobenzoyl)-urea | Fp.: 157–159° C. |
| 1-(2,6-Dichlorobenzoyl)-3-[4-(2,2-dichlorocyclopropylmethoxy)-phenyl]-urea | Fp.: 195–196° C. |
| 1-(2,6-Dichlorobenzoyl)-3-[4-(2,2-dichlorocyclopropylmethoxy)-3,5-dimethylphenyl]-urea | Fp.: 172–173° C. |
| 1-(2,6-Dichlorobenzoyl)-3-[3,5-dichloro-4-(2,2-dichlorocyclopropylmethoxy)-phenyl]-urea | Fp.: 158–160° C. |
| 1-(2-Chlorobenzoyl)-3-[3,5-dichloro-4-(2,2-dichlorocyclopropylmethoxy)-phenyl]-urea | Fp.: 186–187° C. |
| 1-(2-Chloro-6-fluorobenzoyl)-3-[3,5-dichloro-(2,2-dichlorocyclopropylmethoxy)-phenyl]-urea | Fp.: 164–166° C. |
| 1-[3,5-Dichloro-4-(2,2-dichlorocyclopropylmethoxy)-phenyl]-3-(2,6-difluorobenzoyl)-urea | Fp.: 156–157° C. |
| 1-(2-Chlorobenzoyl)-3-[3-chloro-4-(2,2-dichlorocyclopropylmethoxy)-phenyl]-urea | Fp.: 166–168° C. |
| 1-[3-Chloro-4-(2,2-dichlorocyclopropylmethoxy)-phenyl]-3-(2,6-difluorobenzoyl)-urea | Fp.: 166–167° C. |
| 1-[3-Chloro-4-(2,2-dichlorocyclopropylmethoxy)-phenyl]-3-(2-chloro-6-fluorobenzoyl)-urea | Fp.: 164–165° C. |
| 1-[3,5-Dichloro-4-(2,2-dichlorocyclopropylmethoxy)-phenyl]-3-(2-methylbenzoyl)-urea | Fp.: 175–177° C. |
| 1-[3-chloro-4-(2,2-dichlorocyclopropylmethoxy)-phenyl]-3-(2-methylbenzoyl)-urea | Fp.: 200–202° C. |
| 1-[3-Chloro-4-(2,2-dichloro-1-methylcyclopropylmethoxy)-phenyl]-3-(2,6-dichlorobenzoyl)-urea | Fp.: 196–197° C. |
| 1-(2-Chlorobenzoyl)-3-[3-chloro-4-(2,2-dichloro-1-methylcyclopropylmethoxy)-phenyl]-urea | Fp.: 171–173° C. |
| 1-[3-Chloro-4-(2,2-dichloro-1-methylcyclopropylmethoxy)-phenyl]-3-(2-chloro-6-fluorobenzoyl)-urea | Fp.: 210–211° C. |
| 1-[3-Chloro-4-(2,2-dichloro-1-methylcyclopropylmethoxy-phenyl]-3-(2,6-difluorobenzoyl)-urea | Fp.: 192–193° C. |
| 1-[3-Chloro-4-(2,2-dichloro-1-methylcyclopropylmethoxy)-phenyl]-3-(2-methylbenzoyl)-urea | Fp.: 147–148° C. |
| 1-[4-(2,2-Dichloro-1-methylcyclopropylmethoxy)-phenyl]-3-(2,6-dichlorobenzoyl)-urea | Fp.: 187–188° C. |
| 1-(2-Chlorobenzoyl)-3-[4-(2,2-dichloro-1-methylcyclopropylmethoxy)-phenyl]-urea | Fp.: 180–182° C. |
| 1-(2-Chlorobenzoyl)-3-[3,5-dichloro-4-(2,2-dichloro-1-methylcyclopropylmethoxy)-phenyl]-urea | Fp.: 196–197° C. |
| 1-(2-Chlorobenzoyl)-3-[3-chloro-4-(2,2-dichloro-3-methylcyclopropylmethoxy)-phenyl]-urea | Fp.: 183–184° C. |
| 1-(2,6-Dichlorobenzoyl)-3-[3,5-dichloro-4-(2,2-dichloro-1-methylcyclopropylmethoxy)-phenyl]-urea | Fp.: 219–221° C. |
| 1-(2-Chlorobenzoyl)-3-[3-chloro-4-(2,2-dichloro-3-phenylcyclopropylmethoxy)-phenyl]-urea | Fp.: 146–148° C. |
| 1-[3-Chloro-4-(2,2-dichloro-3-phenylcyclopropylmethoxy)-phenyl]-3-(2,6-dichlorobenzoyl)-urea | Fp.: 159–160° C. |
| 1-(2-Chlorobenzoyl)-3-[3,5-dichloro-4-(2,2-dichloro-3-methylcyclopropylmethoxy)-phenyl]-urea | Fp.: 167–168° C. |
| 1-(2,6-Dichlorobenzoyl)-3-[3,5-dichloro-4-(2,2-dichloro-3-methylcyclopropylmethoxy)-phenyl]-urea | Fp.: 147–151° C. |
| 1-[3-(2,2-Dichlorocyclopropylmethoxy)-phenyl]-3-(2,6-difluorobenzoyl)-urea | Fp.: 152–154° C. |
| 1-(2,6-Dichlorobenzoyl)-3-[4-(2,2-dichloro-3-methylcyclopropylmethoxy)-phenyl]-urea | Fp.: 194–195° C. |
| 1-(2-Chlorobenzoyl)-3-[4-(2,2-dichloro-3-methylcyclopropylmethoxy)-phenyl]-urea | Fp.: 179–199° C. |
| 1-(2-Chlorobenzoyl)-3-[4-(2,2-dichlorocyclopropylmethoxy)-3,5-dimethylphenyl]-urea | Fp.: 183–184° C. |
| 1-[4-(2,2-dichlorocyclopropylmethoxy)-3,5-dimethylphenyl]-3-(2,6-difluorobenzoyl)-urea | Fp.: 180–182° C. |
| 1-[4-(2,2-Dichlorocyclopropylmethoxy)-3,5-dimethylphenyl]-3-(2-methylbenzoyl)-urea | Fp.: 175–177° C. |
| 1-(2-Chloro-6-fluorobenzoyl)-3-[ 4-(2,2-dichlorocyclopropylmethoxy)-3,5-dimethylphenyl]-urea | Fp.: 197–199° C. |
| 1-(2-Chlorobenzoyl)-3-[3-(2,2-dichloro-3-methylcyclopropylmethoxy)-phenyl]-urea | Fp.: 147–149° C. |
| 1-(2-Chlorobenzoyl)-3-[4-(2,2-dichloro-3-methylcyclopropylmethoxy)-3,5-dimethylphenyl]-urea | Fp.: 191–192° C. |
| 1-(2,6-Dichlorobenzoyl)-3-[4-(2,2-dichloro-3-methylcyclopropylmethoxy)-3,5-dimethylphenyl]-urea | Fp.: 175–176° C. |
| 1-[4-(2,2-Dichloro-3-methylcyclopropylmethoxy)-3,5-dimethylphenyl]-3-(2-methylbenzoyl)-urea | Fp.: 175–180° C. |
| 1-(2-Chlorobenzoyl)-3-[4-(2,2-dichlorocyclopropylmethoxy)-3-methylphenyl]-urea | Fp.: 169–171° C. |
| 1-(2,6-Dichlorobenzoyl)-3-[4-(2,2-dichlorocyclopropylmethoxy)-3-methylphenyl]-urea | Fp.: 167–168° C. |
| 1-(2-Chlorobenzoyl)-3-[4-(2,2-dichloro-3-methylcyclopropylmethoxy)-3-methylphenyl]-urea | Fp.: 142–143° C. |
| 1-(2,6-Dichlorobenzoyl)-3-[3-(2,2-dichloro-1-methylcyclopropylmethoxy)-phenyl]-urea | Fp.: 174–176° C. |
| 1-(2,6-Dichlorobenzoyl)-3-[4-(2,2-dichloro-3-methylcyclopropylmethoxy)-3-methylphenyl]-urea | Fp.: 138–140° C. |
| 1-(2-Chlorobenzoyl)-3-[4-(2,2-dichloro-1-methylcyclopropylmethoxy)-3-methylphenyl]-urea | Fp.: 163–164° C. |
| 1-(2,6-Dichlorobenzoyl)-3-[4-(2,2-dichloro-1-methylcyclopropylmethoxy)-3-methylphenyl]-urea | Fp.: 162–163° C. |
| 1-(2-Chlorobenzoyl)-3-[4-(2,2-dichloro-1-methyl-cyclopropylmethoxy)-3,5-dimethylphenyl]-urea | Fp.: 185–187° C. |
| 1-(2,6-Dichlorobenzoyl)-3-[4-(2,2-dichloro-1-methylcyclopropylmethoxy)-3,5-dimethylphenyl]-urea | Fp.: 196–197° C. |

The acylureas in accordance with the invention are colorless and odorless crystalline compounds. They dissolve only very little in water and toluene, better in acetic acid ethyl ester and good in dimethylformamide.

The following examples serve to illustrate the application possibilities of the compounds of the present invention in form of its preparations.

EXAMPLE 2

The compounds of the present invention were employed as aqueous suspensions or emulsions with a concentration of the active ingredient of 0.1%.

Dwarf bean plants (*phaseolus vulgaris*) in the primary leaf state were dipped into these preparations containing active ingredients. For each experiment member 4 plant stems with a total of 8 primary leaves were placed into glass vases filled with water and encaged in glass cylinders. Thereafter, into each glass cylinder were counted 5 larvae of the Mexican bean weevil (*Epilachna varivestis*) in the third larvae stage and kept for 5 days in the glass cylinder. The criterium for the determination of effectiveness was the mortality rate of the larvae in % after the 5 day experiment time.

| Name of Compound | Active Ingredient in % | Mortality in % |
|---|---|---|
| 1-[3-Chloro-4-(2,2-dichlorocyclopropylmethoxy-phenyl]-3-(2,6-dichlorobenzoyl)-urea | 0.1 | 100 |
| 1-(2,6-Dichlorobenzoyl)-3-[4-(2,2-dichlorocyclopropylmethoxy)-phenyl]-urea | 0.1 | 100 |
| 1-(2,6-Dichlorobenzoyl)-3-[4-(2,2-dichlorocyclopropylmethoxy)-3,5-dimethylphenyl]-urea | 0.1 | 100 |
| 1-(2,6-Dichlorobenzoyl)-3-[3,5-dichloro-4-(2,2-dichlorocyclopropylmethoxy)-phenyl]-urea | 0.1 | 93 |
| 1-(2-Chlorobenzoyl)-3-[3,5-dichloro-4-(2,2-dichlorocyclopropylmethoxy)-phenyl]-urea | 0.1 | 100 |
| 1-(2-Chloro-6-fluorobenzoyl)-3-[3,5-dichloro-4-(2,2-dichlorocyclopropylmethoxy)-phenyl]-urea | 0.1 | 100 |
| 1-[3,5-Dichloro-4-(2,2-dichlorocyclopropylmethoxy)-phenyl]-3-(2,6-difluorobenzoyl)-urea | 0.1 | 100 |
| 1-(2-Chlorobenzoyl)-3-[3-chloro-4-(2,2-dichlorocyclopropylmethoxy)-phenyl]-urea | 0.1 | 100 |
| 1-[3-Chloro-4-(2,2-dichlorocyclopropylmethoxy)-phenyl]-3-(2,6-difluorobenzoyl)-urea | 0.1 | 100 |
| 1-[3-Chloro-4-(2,2-dichloropropylmethoxy)-phenyl]-3-(2-chloro-6-fluorobenzoyl)-urea | 0.1 | 87 |
| 1-[3,5-Dichloro-4-(2,2-dichlorocyclopropylmethoxy)-phenyl]-3-(2-methylbenzoyl)-urea | 0.1 | 100 |
| 1-[3-Chloro-4-(2,2-dichloro-3-methylcyclopropylmethoxy)-phenyl]-3-(2,6-dichlorobenzoyl)-urea | 0.1 | 87 |
| 1-[3-Chloro-4-(2,2-dichloro-1-methylcyclopropylmethoxy)-phenyl]-3-(2,6-dichlorobenzoyl)-urea | 0.1 | 100 |
| 1-(2-Chlorobenzoyl)-3-[3-chloro-4-(2,2-dichloro-1-methylcyclopropylmethoxy)-phenyl]-urea | 0.1 | 80 |
| 1-[3-Chloro-4-(2,2-dichloro-1-methylcyclopropylmethoxy)-phenyl]-3-(2-chloro-6-fluorobenzoyl)-urea | 0.1 | 100 |
| 1-[Chloro-4-(2,2-dichloro-1-methylcyclopropylmethoxy)-phenyl]-3-(2,6-difluorobenzoyl)-urea | 0.1 | 93 |
| 1-[3-Chloro-4-(2,2-dichloro-1-methylcyclopropylmethoxy)-phenyl]-3-(2-methylbenzoyl)-urea | 0.1 | 80 |
| 1-[4-(2,2-Dichloro-1-methylcyclopropylmethoxy)-phenyl]-3-(2,6-dichlorobenzoyl)-urea | 0.1 | 100 |
| 1-(2-Chlorobenzoyl)-3-[4-(2,2-dichloro-1-methylcyclopropylmethoxy)-phenyl]-urea | 0.1 | 100 |
| 1-(2-Chlorobenzoyl)-3-[3,5-dichloro-4-(2,2-dichloro-1-methylcyclopropylmethoxy)-phenyl]-urea | 0.1 | 100 |
| 1-(2-Chlorobenzoyl)-3-[3-chloro-4-(2,2-dichloro-3-methylcyclopropylmethoxy)-phenyl]-urea | 0.1 | 100 |
| 1-(2,6-Dichlorobenzoyl)-3-[3,5-dichloro-4-(2,2-dichloro-1-methylcyclopropylmethoxy)-phenyl]-urea | 0.1 | 100 |
| 1-(2-Chlorobenzoyl)-3-[3-chloro-4-(2,2-dichloro-3-phenylcyclopropylmethoxy)-phenyl]-urea | 0.1 | 73 |
| 1-[3-Chloro-4-(2,2-dichloro-3-phenylcyclopropylmethoxy)-phenyl]-3-(2,6-dichlorobenzoyl)-urea | 0.1 | 80 |
| 1-(2-Chlorobenzoyl)-3-[3,5-dichloro-4-(2,2-dichloro-3-methylcyclopropylmethoxy)-phenyl]-urea | 0.1 | 100 |
| 1-(2-Chlorobenzoyl)-3-[4-(2,2-dichlorocyclopropylmethoxy)-3-methylphenyl]-urea | 0.1 | 100 |
| 1-(2,6-Dichlorobenzoyl)-3-[4-(2,2-dichlorocyclopropylmethoxy)-3-methylphenyl]-urea | 0.1 | 90 |
| 1-(2-Chlorobenzoyl)-3-[4-(2,2-dichloro-3-methylcyclopropylmethoxy)-3-methylphenyl]-urea | 0.1 | 100 |
| 1-(2,6-Dichlorobenzoyl)-3-[3-(2,2-dichloro-1-methylcyclopropylmethoxy)-phenyl]-urea | 0.1 | 90 |
| 1-(2,6-Dichlorobenzoyl)-3-[4-(2,2-dichloro-3-methylcyclopropylmethoxy)-3-methylphenyl]-urea | 0.1 | 100 |
| 1-(2-Chlorobenzoyl)-3-[4-(2,2-dichloro-1-methylcyclopropylmethoxy)-3-methylphenyl]-urea | 0.1 | 100 |
| 1-(2,6-Dichlorobenzoyl)-3-[4-(2,2-dichloro-1-methylcyclopropylmethoxy)-3-methylphenyl]-urea | 0.1 | 100 |
| 1-(2-Chlorobenzoyl)-3-[4-(2,2-dichloro-1-methylcyclopropylmethoxy)-3,5-dimethylphenyl]-urea | 0.1 | 100 |
| 1-(2,6-Dichlorobenzoyl)-3-[4-(2,2-dichloro-1-methylcyclopropylmethoxy)-3,5-dimethylphenyl]-urea | 0.1 | 90 |
| 1-(2,6-Dichlorobenzoyl)-3-[3,5-dichloro-4-(2,2-dichloro-3-methylcyclopropylmethoxy)-phenyl]-urea | 0.1 | 100 |
| 1-[3-(2,2-Dichlorocyclopropylmethoxy)-phenyl]-3-(2,6-difluorobenzoyl)-urea | 0.1 | 80 |
| 1-(2,6-Dichlorobenzoyl)-3-[ 4-(2,2-dichloro-3-methylcyclopropylmethoxy)-phenyl]-urea | 0.1 | 100 |
| 1-(2-Chlorobenzoyl)-3-[4-(2,2-dichloro-3-methylcyclopropylmethoxy)-phenyl]-urea | 0.1 | 100 |
| 1-(2-Chlorobenzoyl)-3-[4-(2,2-dichlorocyclopropylmethoxy)-3,5-dimethylphenyl]-urea | 0.1 | 100 |
| 1-[4-(2,2-Dichlorocyclopropylmethoxy)-3,5-dimethylphenyl]-3-(2,6-difluorobenzoyl)-urea | 0.1 | 100 |
| 1-[4-(2,2-Dichlorocyclopropylmethoxy)-3,5-dimethylphenyl]-3-(2-methylbenzoyl)-urea | 0.1 | 100 |
| 1-(2-Chloro-6-fluorobenzoyl)-3-[4-(2,2-dichlorocyclopropylmethoxy)-3,5-dimethylphenyl]-urea | 0.1 | 100 |
| 1-(2-Chlorobenzoyl)-3-[3-(2,2-dichloro-3-methylcyclopropylmethoxy)-phenyl]-urea | 0.1 | 73 |
| 1-(2-Chlorobenzoyl)-3-[4-(2,2-dichloro-3-methylcyclopropylmethoxy)-3,5-dimethylphenyl]-urea | 0.1 | 100 |
| 1-(2,6-Dichlorobenzoyl)-3-[4-(2,2-dichloro-3-methylcyclopropylmethoxy-3,5-dimethylphenyl]-urea | 0.1 | 80 |
| 1-[4-(2,2-Dichloro-3-methylcyclopropylmethoxy)-3,5-dimethylphenyl]-3-(2-methylbenzoyl)-urea | 0.1 | 100 |

EXAMPLE 3

The compounds according to the present invention were employed as aqeous suspensions or emulsions with a concentration of the active ingredient of 0.05%. Similarly the comparison materials were prepared as aqueous suspensions. Pro experiment member two cauliflower leaves in polystyrene Petri-dishes were sprayed in measured quantities of 4 mg spraying liquor pro cm². After the beginning of drying of the spray layers 10 young caterpillars of the diamondback moth (*plutella maculipennis*) were counted into each Petri-dish and were exposed to the treated food in the laboratory under long day conditions for five days. The criterium for the determination of effectiveness was the mortality ratio of the caterpillars in % after five days of the experiment.

| Name of Compound | Active Ingredient in % | Mortality in % |
|---|---|---|
| 1-(2,6-Dichlorobenzoyl)-3-[4-(2,2-dichlorocyclopropylmethoxy)-3,5-dimethylphenyl]-urea | 0.05 | 90 |
| 1-(2,6-Dichlorobenzoyl)-3-[3,5-dichloro-4-(2,2-dichlorocyclopropylmethoxy)-phenyl]-urea | 0.05 | 97 |
| 1-(2-Chlorobenzoyl)-3-[3,5-dichloro-4-(2,2-dichlorocyclopropylmethoxy)-phenyl]-urea | 0.05 | 100 |
| 1-(2-Chloro-6-fluorobenzoyl)-3-[3,5-dichloro-4-(2,2-dichlorocyclopropylmethoxy)-phenyl]-urea | 0.05 | 100 |
| 1-[3,5-Dichloro-4-(2,2-dichlorocyclopropylmethoxy)-phenyl]-3-(2,6-difluorobenzoyl)-urea | 0.05 | 100 |
| 1-[3-Chloro-4-(2,2-dichlorocyclopropylmethoxy)-phenyl]-3-(2-chloro-6-fluorobenzoyl)-urea | 0.05 | 93 |
| 1-[3,5-Dichloro-4-(2,2-dichlorocyclopropylmethoxy)-phenyl]-3-(2-methylbenzoyl)-urea | 0.05 | 93 |
| Comparison Compounds (according to German Patent 2,123,236) | | |
| 1-(4-Chlorophenyl)-3-(2,6-dichlorobenzoyl)-urea | 0.05 | 10 |
| 1-(4-Chlorophenyl)-3-(2,6-difluorobenzoyl)-urea | 0.05 | 20 |

EXAMPLE 4

The compounds according to the present invention were employed as aqueous suspensions or emulsions with a concentration of active ingredient of 0.001%. In a like manner, the comparison material was employed as an aqueous suspension.

In each experiment member in a polystyrene Petri-dish 8 leaflet pairs of the broad bean (*Vicia faba*) as well as 10 caterpillars of the Egyptian cotton moth (*Spodoptera littoralis*) in the second larvae stage were sprayed with measured quantities of 4 mg spray liquor pro cm². After beginning of drying of the sprayed layers the Petri-dishes were closed and left for 5 days in the laboratory under long day conditions.

The criterim for the determination of effectiveness was the mortality ratio of the caterpillars in % after 5 days of the experiment.

| Name of Compound | Active Ingredient in % | Mortality in % |
|---|---|---|
| 1-[3,5-Dichloro-4-(2,2-dichlorocyclopropylmethoxy)-phenyl]-3-(2,6-difluorobenzoyl)-urea | 0.001 | 97 |
| 1-(2-Chlorobenzoyl)-3-[3-chloro-4-(2,2-dichlorocyclopropylmethoxy)-phenyl]-urea | 0.001 | 97 |
| 1-[3,5-Dichloro-4-(2,2-dichlorocyclopropylmethoxy)-phenyl]-3-(2-methylbenzoyl)-urea | 0.001 | 97 |
| 1-[3-Chloro-4-(2,2-dichlorocyclopropylmethoxy)-phenyl]-3-(2-methylbenzoyl)-urea | 0.001 | 100 |
| Comparison material (according to German Patent 2,123,236) | | |
| 1-(4-Chlorophenyl)-3-(2,6-difluorobenzoyl)-urea | 0.001 | 73 |

What is claimed is:

1. Acylureas of a composition having the general formula

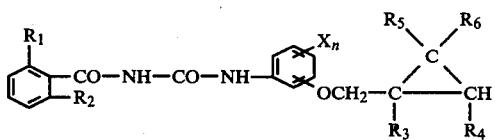

wherein
R₁ is halogen, alkyl with from 1 to 6 carbon atoms, or alkoxy with from 1 to 6 carbon atoms;
R₂ is hydrogen or halogen;
R₃ is hydrogen or alkyl with from 1 to 6 carbon atoms;
R₄ is hydrogen, alkyl with from 1 to 6 carbon atoms, aryl with from 6 to 12 carbon atoms, halogen substituted aryl with from 6 to 12 carbon atoms, or alkaryl with from 7 to 12 carbon atoms;
R₅ is halogen;
R₆ is hydrogen or halogen;
X is halogen or alkyl with from 1 to 6 carbon atoms; and
n is 0, 1 or 2.

2. Acylureas according to claim 1 wherein
R₁ is chlorine or fluorine;
R₂ is chlorine, fluorine or hydrogen;
R₃ is hydrogen or methyl;
R₄ is hydrogen, methyl or phenyl;
R₅ is chlorine, fluorine or bromine;
R₆ is chlorine, bromine, fluorine or hydrogen;
X is chlorine or methyl; and
n is 0, 1 or 2.

3. 1-[3-Chloro-4-(2,2-dichloro-3-methylcyclopropylmethoxy)-phenyl]-3-(2,6-dichlorobenzoyl)-urea.
4. 1-[3-Chloro-4-(2,2-dichlorocyclopropylmethoxy)-phenyl]-3-(2,6-dichlorobenzoyl)-urea.
5. 1-(2,6-Dichlorobenzoyl)-3-[4-(2,2-dichlorocyclopropylmethoxy)-phenyl]-urea.
6. 1-(2,6-Dichlorobenzoyl)-3-[4-(2,2-dichlorocyclopropylmethoxy)-3,5-dimethylphenyl]-urea.
7. 1-(2,6-Dichlorobenzoyl)-3-[3,5-dichloro-4-(2,2-dichlorocyclopropylmethoxy)-phenyl]-urea.
8. 1-(2-Chlorobenzoyl)-3-[3,5-dichloro-4-(2,2-dichlorocyclopropylmethoxy)-phenyl]-urea.
9. 1-(2-Chloro-6-fluorobenzoyl)-3-[3,5-dichloro-4-(2,2-dichlorocyclopropylmethoxy)-phenyl]-urea.
10. 1-[3,5-Dichloro-4-(2,2-dichlorocyclopropylmethoxy)-phenyl]-3-(2,6-difluorobenzoyl)-urea.
11. 1-(2-Chlorobenzoyl)-3-[3-chloro-4-(2,2-dichlorocyclopropylmethoxy)-phenyl]-urea.
12. 1-[3-Chloro-4-(2,2-dichlorocyclopropylmethoxy)phenyl]-3-(2,6-difluorobenzoyl)-urea.
13. 1-[3-Chloro-4-(2,2-dichlorocyclopropylmethoxy)phenyl]-3-(2-chloro-6-fluorobenzoyl)-urea.
14. 1-[3,5-Dichloro-4-(2,2-dichlorocyclopropylmethoxy)phenyl]-3-(2-methylbenzoyl)-urea.
15. 1-[3-Chloro-4-(2,2-dichlorocyclopropylmethoxy)phenyl]-3-(2-methylbenzoyl)-urea.
16. 1-[3-Chloro-4-(2,2-dichloro-1-methylcyclopropylmethoxy)-phenyl]-3-(2,6-dichlorobenzoyl)-urea.
17. 1-(2-Chlorobenzoyl)-3-[3-chloro-4-(2,2-dichloro-1-methylcyclopropylmethoxy)-phenyl]-urea.
18. 1-[3-Chloro-4-(2,2-dichloro-1-methylcyclopropylmethoxy)-phenyl]-3-(2-chloro-6-fluorobenzoyl)-urea.
19. 1-[3-Chloro-4-(2,2-dichloro-1-methylcyclopropylmethoxy)-phenyl]-3-(2,6-difluorobenzoyl)-urea.
20. 1-[3-Chloro-4-(2,2-dichloro-1-methylcyclopropylmethoxy)-phenyl]-3-(2-methylbenzoyl)-urea.
21. 1-[4-(2,2-Dichloro-1-methylcyclopropylmethoxy)phenyl]-3-(2,6-dichlorobenzoyl)-urea.
22. 1-(2-Chlorobenzoyl)-3-[4-(2,2-dichloro-1-methylcyclopropylmethoxy)-phenyl]-urea.
23. 1-(2-Chlorobenzoyl)-3-[3,5-dichloro-4-(2,2-dichloro-1-methylcyclopropylmethoxy)-phenyl]-urea.
24. 1-(2-Chlorobenzoyl)-3-[3-chloro-4-(2,2-dichloro-3-methylcyclopropylmethoxy)-phenyl]-urea.
25. 1-(2,6-Dichlorobenzoyl)-3-[3,5-dichloro-4-(2,2-dichloro-1-methylcyclopropylmethoxy)-phenyl]-urea.
26. 1-(2-Chlorobenzoyl)-3-[3-chloro-4-(2,2-dichloro-3-phenylcyclopropylmethoxy)-phenyl]-urea.
27. 1-[3-Chloro-4-(2,2-dichloro-3-phenylcyclopropylmethoxy)-phenyl]-3-(2,6-dichlorobenzoyl)-urea.
28. 1-(2-Chlorobenzoyl)-3-[3,5-dichloro-4-(2,2-dichloro-3-methylcyclopropylmethoxy)-phenyl]-urea.
29. 1-(2,6-Dichlorobenzoyl)-3-[3,5-dichloro-4-(2,2-dichloro-3-methylcyclopropylmethoxy)-phenyl]-urea.
30. 1-[3-(2,2-Dichlorocyclopropylmethoxy)-phenyl]-3-(2,6-difluorobenzoyl)-urea.
31. 1-(2,6-Dichlorobenzoyl)-3-[4-(2,2-dichloro-3-methylcyclopropylmethoxy)-phenyl]-urea.
32. 1-(2-Chlorobenzoyl)-3-[4-(2,2-dichloro-3-methylcyclopropylmethoxy)-phenyl]-urea.
33. 1-(2-Chlorobenzoyl)-3-[4-(2,2-dichlorocyclopropylmethoxy)-3,5-dimethylphenyl]-urea.
34. 1-[4-(2,2-Dichlorocyclopropylmethoxy)-3,5-dimethylphenyl]-3-(2,6-difluorobenzoyl)-urea.
35. 1-[4-(2,2-Dichlorocyclopropylmethoxy)-3,5-dimethylphenyl]-3-(2-methylbenzoyl)-urea.

36. 1-(2-Chloro-6-fluorobenzoyl)-3-[4-(2,2-dichlorocyclopropylmethoxy)-3,5-dimethylphenyl]-urea.

37. 1-(2-Chlorobenzoyl)-3-[3-(2,2-dichloro-3-methylcyclopropylmethoxy)-phenyl]-urea.

38. 1-(2-Chlorobenzoyl)-3-[4-(2,2-dichloro-3-methylcyclopropylmethoxy)-3,5-dimethylphenyl]-urea.

39. 1-(2,6-Dichlorobenzoyl)-3-[4-(2,2-dichloro-3-methylcyclopropylmethoxy-3,5-dimethylphenyl]-urea.

40. 1-[4-(2,2-Dichloro-3-methylcyclopropylmethoxy)-3,5-dimethylphenyl]-3-(2-methylbenzoyl)-urea.

41. 1-(2-Chlorobenzoyl)-3-[4-(2,2-dichlorocyclopropylmethoxy)-3-methylphenyl]-urea.

42. 1-(2,6-Dichlorobenzoyl)-3-[4-(2,2-dichlorocyclopropylmethoxy)-3-methylphenyl]-urea.

43. 1-(2-Chlorobenzoyl)-3-[4-(2,2-dichloro-3-methylcyclopropylmethoxy)-3-methylphenyl]-urea.

44. 1-(2,6-Dichlorobenzoyl)-3-[3-(2,2-dichloro-1-methylcyclopropylmethoxy)-phenyl]-urea.

45. 1-(2,6-Dichlorobenzoyl)-3-[4-(2,2-dichloro-3-methylcyclopropylmethoxy)-3-methylphenyl]-urea.

46. 1-(2-Chlorobenzoyl)-3-[4-(2,2-dichloro-1-methylcyclopropylmethoxy)-3-methylphenyl]-urea.

47. 1-(2,6-Dichlorobenzoyl)-3-[4-(2,2-dichloro-1-methylcyclopropylmethoxy)-3-methylphenyl]-urea.

48. 1-(2-Chlorobenzoyl)-3-[4-(2,2-dichloro-1-methylcyclopropylmethoxy)-3,5-dimethylphenyl]-urea.

49. 1-(2,6-Dichlorobenzoyl)-3-[4-(2,2-dichloro-1-methylcyclopropylmethoxy)-3,5-dimethylphenyl]-urea.

50. A composition having insecticidal activity comprising
a carrier and/or auxiliary materials; and an insecticidally effective amount of acylureas of the general formula

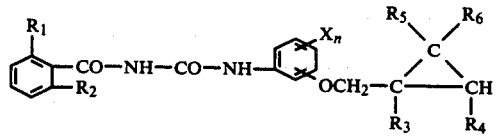

wherein
$R_1$ is hydrogen, alkyl with from 1 to 6 carbon atoms, or alkoxy with from 1 to 6 carbon atoms;
$R_2$ is hydrogen or halogen;
$R_3$ is hydrogen or alkyl with from 1 to 6 carbon atoms;
$R_4$ is hydrogen, alkyl with from 1 to 6 carbon atoms, aryl with from 6 to 12 carbon atoms, halogen substituted aryl with from 6 to 12 carbon atoms, or alkaryl with from 7 to 12 carbon atoms;
$R_5$ is halogen;
$R_6$ is hydrogen or halogen;
X is halogen or alkyl with from 1 to 6 carbon atoms; and
n is 0, 1 or 2.

51. A method for killing and/or eliminating insects comprising
placing in the possible pathway of the insects a composition having an effective insecticidal amount of the compound of the general formula

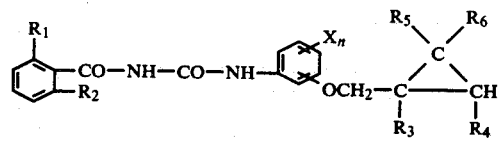

wherein
$R_1$ is hydrogen, alkyl with from 1 to 6 carbon atoms, or alkoxy with from 1 to 6 carbon atoms;
$R_2$ is hydrogen or halogen;
$R_3$ is hydrogen or alkyl with from 1 to 6 carbon atoms;
$R_4$ is hydrogen, alkyl with from 1 to 6 carbon atoms, aryl with from 6 to 12 carbon atoms, halogen substituted aryl with from 6 to 12 carbon atoms, or alkaryl with from 7 to 12 carbon atoms;
$R_5$ is halogen;
$R_6$ is hydrogen or halogen;
X is halogen or alkyl with from 1 to 6 carbon atoms; and
n is 0, 1 or 2.

52. The method of claim 51 wherein the insects are diptera, coleoptera and/or lepidoptera.

* * * * *